Figure 1:
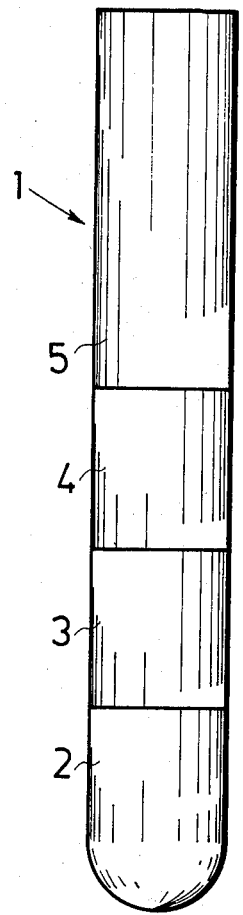

United States Patent [19]

Vihko

[11] 4,272,478
[45] Jun. 9, 1981

[54] DISCARDABLE REACTION RECEPTACLE FOR USE IN IMMUNOLOGICAL ASSAY

[76] Inventor: Reijo Vihko, Jaakonkuja 1 E 3, 90230 Oulu 23, Finland

[21] Appl. No.: 13,315

[22] Filed: Feb. 21, 1979

[30] Foreign Application Priority Data

Feb. 27, 1978 [FI] Finland .............................. 780656

[51] Int. Cl.³ .......................................... G01N 33/50
[52] U.S. Cl. ...................................... 422/57; 23/915;
 23/920; 422/58; 422/102; 435/296
[58] Field of Search .......................... 422/102, 57, 58;
 23/230 B, 915, 920; 435/296, 810

[56] References Cited

U.S. PATENT DOCUMENTS

| | | | |
|---|---|---|---|
| 3,646,346 | 2/1972 | Catt | 23/920 X |
| 3,807,955 | 4/1974 | Note, Jr. et al. | 422/102 X |
| 3,825,410 | 7/1974 | Bagshawe | 422/102 X |
| 4,073,693 | 2/1978 | Janin | 422/102 X |
| 4,147,752 | 4/1979 | Suovaniemi et al. | 23/915 X |

Primary Examiner—Arnold Turk
Attorney, Agent, or Firm—Haseltine and Lake

[57] ABSTRACT

A discardable reaction receptacle for use in immunological assay has been provided, the immunological assay involves reactions between substances derived from patients, labelling substances and antibodies, the last-mentioned being made to adhere to the surface of the receptacle so as to bind the reaction products thereon. The receptacle is constructed so that it consists of mutually detachably connected parts carrying on their surfaces different antibodies, which enable a simultaneous determination of several substances to be performed from a single sample contained in the receptacle.

4 Claims, 3 Drawing Figures

U.S. Patent  Jun. 9, 1981  4,272,478

DISCARDABLE REACTION RECEPTACLE FOR USE IN IMMUNOLOGICAL ASSAY

The present invention concerns a discardable reaction receptacle for use in immunological assay and intended for accomplishing the reactions between the substance to be measured, a labelling substance and the antibody, and which carries affixed to its surface, antibody serving to bind the reaction products to the reaction receptacle.

Immunoassay procedures are employed to determine quantitatively the compounds contained in serum samples obtained from patients, in hospital and research laboratories in particular. By the aid of the determinations information is gained concerning the diseases, if any, which are present in the patient, or such determinations may be part of examinations associated with the monitoring of pregnancy, for instance. Nowadays the most important immunological analytic method consists of the radioimmunological method (RIA), which is based on the use of a radioactively labeled substance. Other, non-radioactive labelling procedures are also possible in principle, but for the time being, at least, their significance in practice is minor, owing to their lower sensitivity.

Immunological methods of analysis are based on a reaction taking place between the substance to be measured, which is obtained from the patient, and an antagonistic agent, for instance between a so-called antigen and a so-called antibody, and in which reaction an insoluble complex is produced as its result. In the role of radioactive label, molecules almost identical with those of the substance to be measured or with the antibody are used, which have usually been labelled with iodine-125 or with tritium. The labelling has no effect on the chemical properties of the molecule, and the result of the determination is obtained by recording the radiation emitted by the label which participated in the reaction. Numerous substances occurring in biological samples may be considered as substances to be measured, including hormones, proteins, drugs and vitamins. The antibodies are then protein molecules, which are manufactured with the aid of experimental animals, such as rabbits, for instance. The particular advantage of the radioimmunological method is its high sensitivity, which renders possible the accurate and specific analysis of substance quantities even as small as on the order of $10^{-12}$ g.

In practice, radioimmunological determinations are carried out, using ready-made reagent sets containing, among other things, the antibody and the labelling substance. The substance to be measured is obtained in the patient's blood sample, from which are separation of the red blood cells the serum is transferred into a reaction receptacle. If the label is chemically equivalent with the substance to be measured, it is added into the reaction receptacle together with the antibody. On the other hand, nowadays such test tubes are also used as reaction receptacles in which the antibody, for instance, has already been fixed on the inside of the tube. In that case the serum contained in the substance to be measured and the label substance are introduced in the test tube and the complex compounds formed as reaction products will be bound to the walls of the tube, the radioactivity of this wall being measured after the label which did not react has been removed. If a radioactively labelled antibody is used as labelling substance, the reactions have to be carried out in two steps, in that the substance to be measured is first allowed to become fixed to the tube, and in the next step labelling substance is introduced into the tube and this substance is further bound to the substance under measurement.

Antibodies appropriate for use in immunological determinations are characterized by very high specificity, that is the capacity of reacting only with a given substance, that which is the object of measurement. Similarly, each particular substance to be measured requires its own reagent set, and in instances in which one desires to measure a great number of different substances, the number of determinations to be carried out will be high. The object of the present invention is to eliminate this drawback by rendering possible the simultaneous determination of several substances, whereby the diagnoses and other examinations carried out by laboratories are speeded up altogether decisively in this respect. The invention is characterized in that the reaction receptacle consists of components detachably joined together and the surfaces of which carry different antibodies so that several substances to be measured are simultaneously determinable from one and the same sample held in the reaction receptacle. Different substances will then be bound to different parts of the reaction receptacle, in accordance with the antibody affixed to each particular part; after the reaction has taken place, the parts are detached from each other for measurement of radioactivity. It is, for instance, possible in the monitoring of pregnancy to determine the well-being of the foetus, congenital diseases, if any, or potential twin pregnancy on the basis of certain substances present in the mother's blood, and all these substances may be simultaneously determined when the reaction receptacle of the invention is used.

A favourable embodiment of the invention is characterized in that the reaction receptacle is composed of tubular sections. The reaction receptacle may then comprise consecutive tubular sections, of which the inner surfaces have been partly or totally coated with various antibodies. A reaction receptacle of this type resembles a common test tube, and its use is just as convenient. It is possible, on the other hand, to compose the reaction receptacle of concentric components, the inner surface of the outer, tubular component and the outer surface of the inner component carrying different antibodies.

Figure 2:
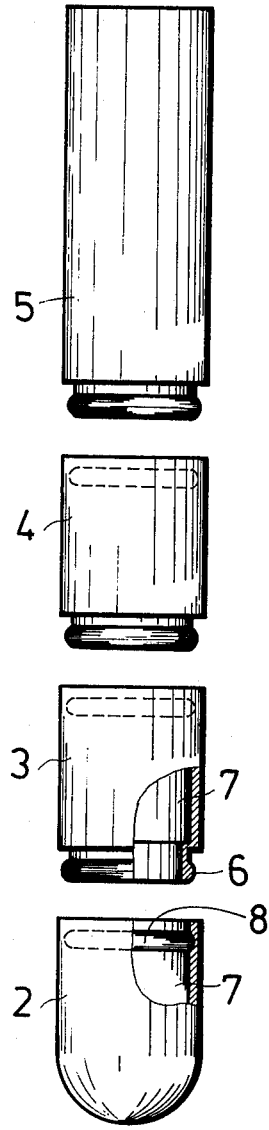
Figure 3:
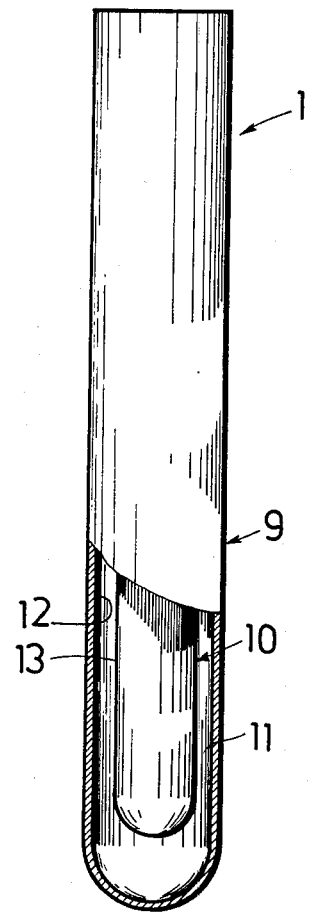

The invention is described in the following in detail with the aid of examples, with reference being made to the attached drawing, wherein:

FIG. 1 presents a reaction receptacle composed of consecutive tubular parts,

FIG. 2 shows the reaction receptacle of FIG. 1, its parts detached from each other, and FIG. 3 shows, partly sectioned, a reaction receptacle composed of components placed within each other.

Referring now to FIG. 1, this presents a discardable reaction receptacle 1 for use in radioimmunoassay, this receptacle consisting of four consecutive tubular sections 2 through 5, which are detachable from each other as FIG. 2 shows. The parts join each other integrally by the joint members 6, which are part of the components 3–5, and by the annular grooves 8 in the inner surfaces 7 of parts 2–4. The reaction receptacle is preferably made of plastic material, which ensures that the sections 2–5 are easy to pull apart.

The reaction receptacle of FIG. 3 consists of two components, 9 and 10, disposed within each other and the reaction taking place in the volume 11 remaining between the two. The components may be attached to each other, for instance, by means of joining members stretched between the inner surface 12 of the outer, tubular component 9 and the outer surface 13 of the inner component 10, although no such members have been depicted in the figure. The most important consideration in such connections is that the detachment of the components, 9 and 10, from each other shall be easy and convenient.

Radioimmunoassays are in the first place based on the reactions taking place between the measurable substances present in the blood, their specific antibodies and radioactive labelling substances. A reaction receptacle as shown in FIG. 3 may be used to carry out simultaneous assays of two, and the receptacle of FIG. 1, even up to four different substances to be measured. In the receptacle of FIG. 3, two different antibodies have been made adherent to the inner surface 12 of the outer component 9 and to the outer surface 13 of the inner component 10, respectively, each binding to itself a specific antigen and label. Upon completed reaction, the components 9 and 10 are detached from each other and the radiation emitted by each is separately recorded. Similarly, in the reaction receptacle of FIG. 1 the different antibodies have been affixed on the inner surface 7 of the receptacle so that of the sections 2–5 each binds its own antigen.

As examples of such combinations of substances in the assay of which the reaction receptacle of the invention may be used, there may be mentioned: estriol ($E_3$), the lactogenic placental hormone (HPL) and alfa-fetoprotein ($\alpha$-FP), on the basis of which the well-being of the foetus is assessed; thyroxin ($T_4$), triiodothyronine ($T_3$) and thyroid stimulating hormone (TSH), which form a basis for assessment of the thyroid function; and phenytoin, carbamazepine, phenobarbital and ethosuccimide, which enable the therapy of epilepsy to be monitored.

It is obvious to a person skilled in the art that various embodiments of the invention are not confined to the examples presented in the foregoing but may vary within the scope of the claims following below. For instance, the substances and combinations of substances suitable to be the object of assay are by no means confined to those mentioned above: any other substances may be equally considered which are immunologically determinable. It is further possible to make such arrangements that the substance affixed to the surface of the reaction receptacle, which has been generally specified as "antibody" in the claims, may as well be an antigen.

The invention is not confined to radioimmunological assays (RIA) either and it may also be employed in immunoradiometric assays (IRMA), or even in such procedures in which the labelling agent is not radioactive. The reaction receptacle itself may also deviate from that which has been presented above. For instance, the number of detachable parts belonging to the receptacle is not confined in any way. It is possible in the design of FIG. 3, if desired, to compose the outer as well as the inner part of detachable sections carrying various antibodies on their surfaces. The inner part need not either be such as shown in the figure: for instance rod-like or annular pieces may also be considered, of which any desired number may be placed in the reaction volume defined by the outer tube.

I claim:

1. In a discardable reaction receptacle for use in immunological assay and intended for the performing of reactions between a substance to be measured, a labelling substance and an antibody, the improvement wherein said reaction receptacle consists essentially of mutually detachably connected parts forming the walls of the receptacle and comprising an outside wall formed by at least one of said parts and defining a space for the reactions to take place, said space being left open from one end, and said mutually detachably connected parts carrying different kinds of antibodies fixed to their surfaces for the purpose of binding different reaction products so as to permit simultaneous determination of several substances from one and the same sample, at least one of the antibodies being fixed to the inner surface of a part which forms said outside wall or a section of it.

2. A receptacle according to claim 1, wherein the outside wall of the receptacle is in the shape of a tube.

3. A receptacle according to claim 2, wherein the receptable consists of consecutive tubular parts, of which the inner surfaces have been totally or partially coated with different antibodies.

4. A receptacle according to claim 2, wherein the receptacle consists of an outer tubular part forming said outside wall and an inner part placed therein, different antibodies being carried on the inner surface of the outer part and on the outer surface of the inner part.

* * * * *